United States Patent [19]

Grueninger

[11] Patent Number: 5,640,437
[45] Date of Patent: Jun. 17, 1997

[54] GONIOMETER

[75] Inventor: Hans-Wolfgang Grueninger, Kriftel, Germany

[73] Assignee: Daimler-Benz Aktiengesellschaft, Stuttgart, Germany

[21] Appl. No.: 507,246

[22] PCT Filed: Feb. 16, 1994

[86] PCT No.: PCT/EP94/00442

§ 371 Date: Aug. 18, 1995

§ 102(e) Date: Aug. 18, 1995

[87] PCT Pub. No.: WO94/19682

PCT Pub. Date: Sep. 1, 1994

[30] Foreign Application Priority Data

Feb. 18, 1993 [DE] Germany ............... 43 04 938

[51] Int. Cl.⁶ .................................................. G01N 23/207
[52] U.S. Cl. ................. 378/81; 378/90; 378/46
[58] Field of Search ................. 378/81, 79, 71, 378/86, 90, 44, 46

[56] References Cited

U.S. PATENT DOCUMENTS

| | | |
|---|---|---|
| 3,344,274 | 9/1967 | Ashby et al. . |
| 3,903,414 | 9/1975 | Herbstein et al. ............ 378/46 |
| 4,263,510 | 4/1981 | Ciccarelli et al. ............ 378/81 X |
| 4,764,945 | 8/1988 | Tadahiro . |
| 4,946,720 | 8/1990 | Yamamoto et al. ............ 378/46 X |
| 4,959,848 | 9/1990 | Parobek . |
| 5,249,216 | 9/1993 | Ohsugi et al. ............ 378/46 |
| 5,406,608 | 4/1995 | Yellepeddi et al. ............ 378/46 |

FOREIGN PATENT DOCUMENTS

| | | |
|---|---|---|
| 0183043 | 6/1986 | European Pat. Off. . |
| 0523566 | 1/1993 | European Pat. Off. . |
| 3441539 | 5/1986 | Germany . |
| 4311440 | 5/1968 | Japan ............ 378/46 |
| 2191284 | 12/1987 | United Kingdom . |
| 94/19682 | 9/1994 | WIPO . |

OTHER PUBLICATIONS

C. Malgrange et al.: "X-ray standing wave technique-Application to the study of surfaces and interfaces". In: Nuclear Instruments and Methods in Physics Research A314 (1992) pp. 285-296.

*Primary Examiner*—David P. Porta
*Attorney, Agent, or Firm*—Spencer & Frank

[57] ABSTRACT

In a goniometer having several axes around which a crystal specimen to be examined can be rotated, a radiation source, a detector for Bragg reflections and a detector for fluorescence radiation, with the detector making it possible to measure lattice geometry and chemical composition at the same time. The detector for the fluorescence radiation is secured in a holder, and is oriented with its surface parallel to the specimen and is pivotably secured together with the specimen to the specimen table. As such, reflexes can be simultaneously observed using the Bragg detector which is secured in a pivotable arm, and the fluorescence radiation using the fluorescence detector.

10 Claims, 1 Drawing Sheet

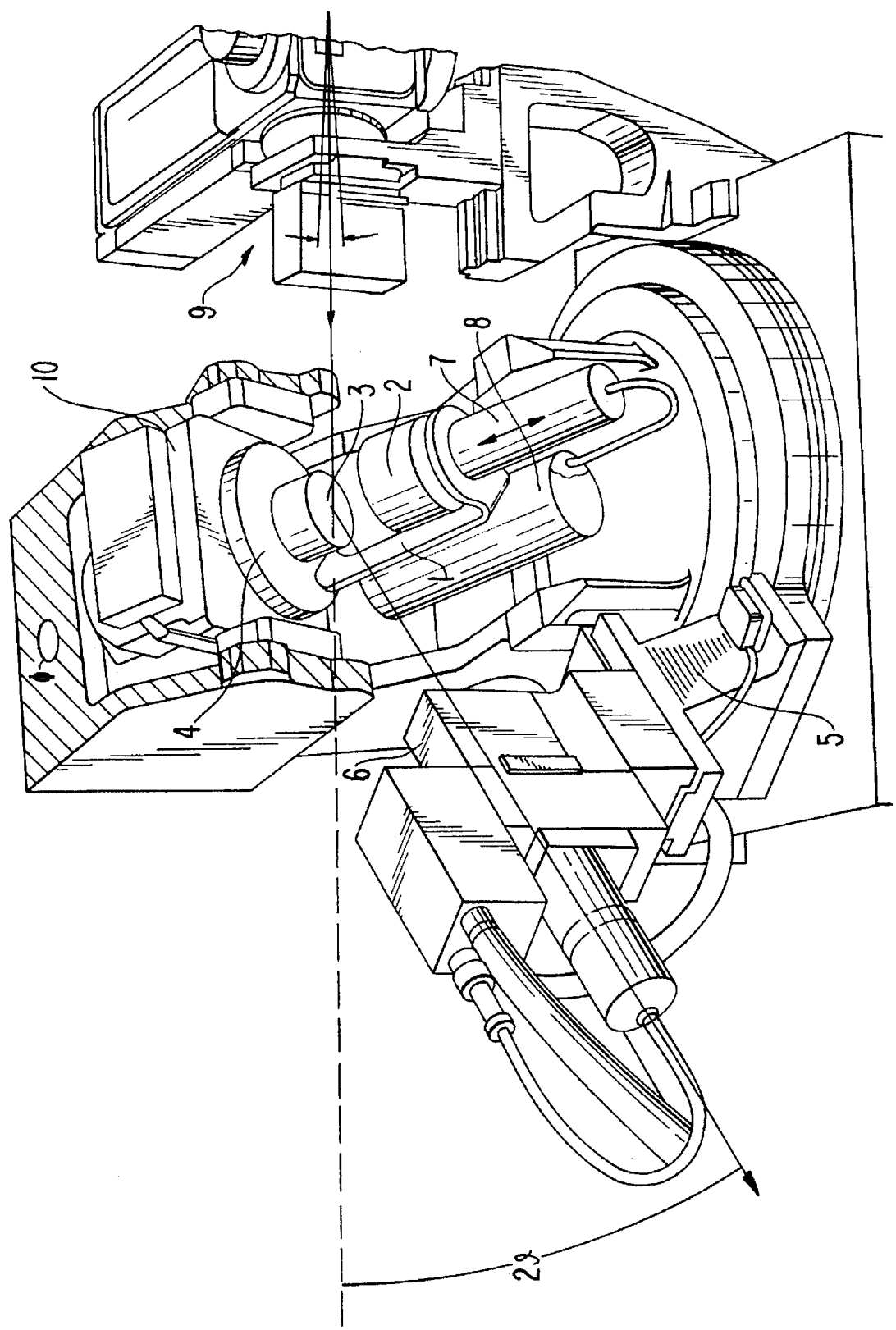

GONIOMETER

BACKGROUND OF THE INVENTION

The invention is based on a goniometer having: a plurality of axes around which a crystal specimen to be examined can be rotated; a radiation source; a detector for Bragg reflections; and a detector for fluorescence radiation.

Such goniometers are known for the structural analysis of crystalline materials. Normally and the lattice constant, the crystal orientation (and for many materials, the texture) are determined. The preferred radiation is the x-radiation of the $K_\alpha$-lines of copper, molybdenum and other metals. The goniometers used for this purpose are comprised of a radiation source, a specimen table which is pivotable around three axes, with the specimen being secured to the table and, secured on an arm, and a detector with which those parts of the space can be scanned in which reflexes are to be expected.

From the publication "X-ray standing wave technique Application to the study of surfaces and interfaces" by C. Malgrange and D. Ferret in Nuclear Instruments and Methods in Physics Research A 314 (1992), p. 285–296, North-Holland, a method is known by means of which the localization of atoms in crystals and on crystal faces can be determined. This method makes use of the fact that in Bragg reflections standing waves are generated which lead to a strong excitation of fluorescence radiation of the atoms which are attached to or embedded in the lattice.

The variation of the fluorescence intensity as a function of the angle position within the Bragg range makes it possible to determine a space coordinate of the foreign atom. From three linear, independent Bragg reflexes, three space coordinates of the foreign atom can be obtained, and thus a precise localization in the host lattice can be had.

It became evident, however, that it is difficult in practice to determine all three space coordinates of the foreign atoms. This is often due to equipment conditions. The specimen must be rotatable in space around three axes to allow non-coplanar lattice planes to be brought to reflection. The fluorescence radiation occurring during the passage through a Rocking curve often is very weak so that, for the recording of this radiation, the energy-dispersive detector must be brought close to the surface of the specimen.

The possible detectors, i.e., SI(LI) or Ge(Li) semiconductor detectors cooled with liquid $N_2$, are voluminous and heavy. Because of the spatial overlapping of the individual detectors, these cannot be brought close enough to the specimen.

Further, the equipment used for this method is awkward in its operation and does not utilize the entire available solid angle for the detectors.

SUMMARY OF THE INVENTION

It is the object of the invention to provide a goniometer as defined above such that it is handy, easy to operate and ready for operation within a short time. The functions must be easy to control and it must be possible to pass through the entire available solid angle range. Furthermore, the detectors are cooled effectively and in a space-saving manner.

This object is solved according to the invention by the features of securing the fluorescence detector to the table via the holder so that the fluorescence detector is pivotable with the table and the crystal specimen around the three axes. The Bragg detector and the fluorescence detector simultaneously observe the reflexes and the fluorescence radiation so as to simultaneously measure lattice geometry and chemical composition of the crystal specimen.

The subject matter of the invention has the advantages that, in particular, by means of a space-saving, light cooling unit which is also configured to be movable, the fluorescence detector can be carried along with the goniometer arm on which the fluorescence detector is secured. This cooler does not need any refill containers for the cooling medium and is instantly ready for operation. Moreover, it also adaptable to a small detector end face and thus makes it possible to go close to the specimen.

The invention is also suitable for the structural determination of adsorbed monolayers of atoms at single-crystalline lattice planes. The method allows a determination of all three space coordinates of the fluorescent atoms.

Moreover, it is possible to cover the entire solid angle range for the Bragg scattering and the fluorescence scattering in one or, at most, two passes. In this process, modifications of the goniometer are limited to a minimum because, at most, a shifting of the fluorescence detector may be necessary so that the range shaded by the fluorescence detector can then also be covered by the Bragg detector.

Through a reduction in size of the radiation detectors, the following can be achieved: By largely reducing volume and weight, it becomes possible to secure the detector together with the specimen on the specimen holder which can be rotated around three axes and to thus bring the detector close to the surface which needs to be examined.

The reduction in size predominantly relates to the cooling unit. Small electrically driven cooling units, functioning, for example, according to the Sterling principle, are particularly advantageous because of their small size. A supply of liquid $N_2$ is not necessary. The semiconductor detector is mounted with a preamplifier on a cooling finger. A vacuum jacket for low-temperature insulation comprises an inlet window for the radiation.

Because of the small half-width of the Rocking curve of almost perfect single crystals, only high-resolution x-ray goniometers can be used. Since the specimen must be oriented in space, the goniometer used is preferably a four-ring goniometer. In accordance with the measuring requirements, a suitable detector can then be secured to one of the three axes of the specimen holder. The most flexible solution probably is a securing at the chi ring of such a diffractometer. When the specimen is moved, the detector stays in a defined position relative to the surface of the specimen. Also, with this arrangement, the diffraction geometry is least influenced. A device for setting the distance of the specimen surface from the detector must be provided. A securing of the detector to the phi or theta axis is also advantageous. But the detector may possibly have to be shifted if the specimen is moved.

BRIEF DESCRIPTION OF THE DRAWINGS

The invention is now explained by way of an embodiment with reference to the drawing, which is a perspective, sectional view of a goniometer according to the invention.

DETAILED DESCRIPTION OF THE INVENTION

The drawing shows a goniometer which has been modified according to the invention. The specimen 3 is secured on the specimen table 4 and can be pivoted in three axes relative to the ray, which is incident here from the right.

In the usual manner, a Bragg detector 6 is provided which is movable on an arm 5 and scans the available space.

Preferably, this takes place in a computer-controlled manner by means of stepping motors and angle decoding. Together with the first stage of the preamplifier, the fluorescence detector 2 is secured on a cooling finger 7 which is supplied with a cooling medium by a compressor 8. Together with its holder 1, the fluorescence detector 2 is secured to the specimen table 4 (phi ring) such that it is pivoted together with the specimen table. The detector 2 secured in the holder 1 is oriented with its surface (inlet window) preferably parallel to specimen 3 and brought as close as possible to the specimen. By moving the fluorescence detector 2 in the direction of the arrow (see FIGURE) in a preferred embodiment of the invention, the distance to specimen 3 is selected to be as small as possible and is adjusted to the angles of arrival and of radiation so that the radiation can reach the specimen and get into the Bragg detector 6 from there.

The fluorescence detector 2 may possibly disturb the measuring process of the Bragg detector 6. Therefore, a further advantageous embodiment of the invention proposes to swing the fluorescence detector slightly sideways so that the desired solid angle range can then be covered by the Bragg detector 6 in a second pass. But because of the symmetry of the Bragg reflexes, it is not necessary to cover the entire half-space. Only the information from one quarter of the entire solid angle is needed and then the fluorescence radiation can be detected from the remaining accessible solid angle range.

Alternatively, the fluorescence detector may also be secured on the pivotable arm 10 (chi ring).

An x-ray tube may be used as radiation source 9. But because of the intensity it is particularly advantageous to use synchrotron radiation. Here, the same arrangement can be used.

The fluorescence detector is comprised of a lithium-drifted silicon or germanium crystal which is enclosed in an evacuated housing while secured to a cooling finger. The x-ray fluorescence radiation is incident through a beryllium window onto the detector crystal in the vacuum chamber. The crystal is cooled just as the first stage of the preamplifier. The detector crystal is secured with its rear side directly on the cooling finger, if possible. With the Stirling cooler used here, $-170°$ C. and below can be reached within a short time.

The following describes the measuring process at a crystal specimen. First, the Rocking curve (Bragg peak) of a selected reflex is measured and, from this, the exact position $\theta_B$ and the half-width $\theta_B$ of the peak are determined. In a second pass, the angle range $\theta_B + \theta_B$ is passed through in small angle steps and the fluorescence radiation of the excited foreign atoms is recorded by means of a multichannel analyzer. From the intensity curve of the radiation as a function of the angle position, the locus coordinate of the fluorescent atom in a direction which is perpendicular to the lattice plane of the reflex can then be determined—as described in the literature—(Malfrange et al.).

If this procedure is repeated with two further independent reflexes, one obtains three coordinates for the spatial fixing of the atom within the host lattice.

What is claimed is:

1. A goniometer, comprising: a specimen table having a crystal specimen securable thereto, said table being pivotable around at least three axes;

a radiation source positioned relative to said table so as to direct radiation toward the crystal specimen;

a pivotable arm located adjacent to said specimen table;

a Bragg detector secured to said pivotable arm for detecting Bragg reflections and observing reflexes from the crystal specimen;

a holder connected to said specimen table; and a fluorescence detector located in said holder and having an inlet window oriented parallel to the specimen for receiving and detecting fluorescence radiation, said fluorescence detector being secured to said table via said holder so as to be pivotable with said table and the crystal specimen around the three axes, said Bragg detector and said fluorescence detector simultaneously observing the reflexes and the fluorescence radiation so as to simultaneously measure lattice geometry and chemical composition of the crystal specimen.

2. The goniometer defined in claim 13, wherein said Bragg detector is pivotable over an angle range that includes a position of said fluorescence detector and said holder, said Bragg detector being movable in a first measuring pass over a portion of the angle range that is free of said fluorescence detector and said holder, said fluorescence detector and said holder being placeable in a new position located in the portion of the angle range covered by said Bragg detector in the first measuring pass so that said Bragg detector can be moved over a remaining portion of the angle range in a second measuring pass.

3. The goniometer defined in claim 1, wherein a space between the crystal specimen and said Bragg detector and said fluorescence detector includes a half-space into which radiation from the crystal specimen is emitted for detection by said Bragg detector and said fluorescence detector, wherein said Bragg detector sweeps an upper portion of the half-space, and said fluorescence detector simultaneously measures the fluorescence radiation in a lower portion of the half-space.

4. The goniometer defined in claim 1, wherein said fluorescence detector is separated from the crystal specimen by a distance selected so that the radiation emitted from said radiation source and the Bragg reflections are not blocked.

5. The goniometer defined in claim 1, wherein said radiation source comprises an x-ray tube.

6. The goniometer defined in claim 1, wherein the radiation from said radiation source is synchrotron radiation.

7. The goniometer defined in claim 1, further comprising a cooling finger having an end face secured to said fluorescence detector for cooling said fluorescence detector down to at least $-70°$ C.

8. The goniometer defined in claim 1, further comprising a Stirling cooler attached to said fluorescence detector for cooling said fluorescence detector.

9. The goniometer defined in claim 1, wherein said fluorescence detector is small and is separated from the crystal specimen by a small distance.

10. The goniometer defined in claim 1, further comprising a cooling finger secured to said fluorescence detector for cooling said fluorescence detector, said cooling finger having a Stirling element arranged therein to effect an adiabatic expansion of a cooling medium; and a compressor connected to said cooling finger via a line, wherein the cooling medium comprises a gas that is compressed by said compressor and fed via the line to said cooling finger for the adiabatic expansion, and returned to said compressor via the same line.

* * * * *